United States Patent
Bombarda et al.

(10) Patent No.: US 9,815,774 B1
(45) Date of Patent: Nov. 14, 2017

(54) HYDRODABCYL

(71) Applicant: Universität Bayreuth, Bayreuth (DE)

(72) Inventors: Elisa Bombarda, Eckersdorf (DE); Oxana Kempf, Kulmbach (DE); Karl Kempf, Kulmbach (DE); Rainer Schobert, Bayreuth (DE); G. Matthias Ullmann, Eckersdorf (DE)

(73) Assignee: UNIVERSITÄT BAYREUTH, Bayreuth (DE)

( * ) Notice: Subject to any disclaimer, the term of this patent is extended or adjusted under 35 U.S.C. 154(b) by 0 days.

(21) Appl. No.: 15/529,700

(22) PCT Filed: Nov. 27, 2015

(86) PCT No.: PCT/EP2015/077982
§ 371 (c)(1),
(2) Date: May 25, 2017

(87) PCT Pub. No.: WO2016/083611
PCT Pub. Date: Jun. 2, 2016

(30) Foreign Application Priority Data

Nov. 28, 2014 (EP) ..................................... 14195529
Dec. 10, 2014 (EP) ..................................... 14197181

(51) Int. Cl.
*C07C 245/08* (2006.01)
*G01N 21/64* (2006.01)
*C09B 29/08* (2006.01)

(52) U.S. Cl.
CPC .......... *C07C 245/08* (2013.01); *C09B 29/081* (2013.01); *G01N 21/64* (2013.01)

(58) Field of Classification Search
None
See application file for complete search history.

(56) References Cited

PUBLICATIONS

International Search Report and Written opinion were dated Aug. 2, 2016 by the International Searching Authority for International Application No. PCT/EP2015/077982, which was filed on Nov. 27, 2015 and published as WO/2016/083611 on Jun. 2, 2016 (Applicant-Universität Bayreuth ) (7 pages).
Monica Alvarado-Gonzalez et al: "TD-DFT /IEFPCM determination of the absorption and emission spectra of DABCYL", Journal of Molecular Structure: Theochem, (2010) vol. 945, No. 1-3, pp. 101-103.
Mayatoshi E.D., et al., "Fluorogenic substrates for assaying retroviral proteases by resonance energy transfer". Science, 1990, 247, 954-958.
Tyagi S. et al., "Molecular Beacons: probes that fluoresce upon hybridization". Nat. Biotech. (1996) 14, 303-308.
Holskin BP.,et al., "A continuous fluorescence-based assay of human cytomegalovirus protease using a peptide substrate". Analytical Biochemistry 227(1):148-55.
Loudwig S. et al. "Photoisomerization of an individual azobenzene molecule in water: an on-off switch triggered by light at a fixed wavelength". J. Am. Chem. Soc. (2006) 126,12404-12405.

*Primary Examiner* — Kamal Saeed
(74) *Attorney, Agent, or Firm* — Ballard Spahr LLP

(57) ABSTRACT

A new azobenzene-based fluorescence quencher with excellent solubility in aqueous solution is described here. This compound represents an optimized alternative to dabcyl in a variety of biomolecular applications, like fluorogenic protease substrates or nucleic acids probes.

10 Claims, 16 Drawing Sheets

HYDRODABCYL

CROSS-REFERENCE TO RELATED APPLICATIONS

This application is a U.S. National Phase Application of International Application No. PCT/EP2015/077982, filed Nov. 27, 2015, which claims priority to European Application No. 14195529.4, filed Nov. 28, 2014, and European Application No. 14197181.2, filed Dec. 10, 2014, each of which are hereby incorporated by reference in their entirety.

FIELD OF INVENTION

The present invention concerns the provision of a novel dark quencher, called Hydrodabcyl, which is water-soluble and suitable for assembling a fluorogenic probe for in vivo as well as in vitro application. The present invention also concerns a method of preparing Hydrodabcyl and the use of Hydrodabcyl as a dark quencher in biological systems.

BACKGROUND

Biomolecular processes are extensively studied by employing fluorescent dyes that either bind non-covalently to a target in the system or, to gain specificity, are covalently linked to the investigated biomolecule. Changes in fluorescence intensity or wavelength indicate that a biochemical event has taken place. There is a large choice of fluorescent dyes whose signal is affected by several physico-chemical parameters, such as pH, hydrophobicity, oxidation state or ionic strength. To improve the strategy of using probes comprising a single label, quencher dyes have been developed to provide dual-labeled probes, in which the quencher is paired with the reporter dye to enhance the observable change in fluorescence. Typically, these probes have a closed (i.e. quenched) form in which the reporter and the quencher are close to each other in space and an open form (i.e. fluorescent) in which the reporter and the quencher are spatially separated.

The quencher can be a second fluorescent dye. In this case, the fluorescence of the reporter can be monitored alone, or both the increase in the fluorescence of the quencher and the decrease in fluorescence of the reporter are observed. An overlap between quencher and reporter fluorescence spectra may cause background noise, which necessitates dedicated care in the instrumental set-up and data analysis as well.

Dark quenchers (e.g. non-fluorescent dyes) offer a solution to this problem because they do not occupy an emission bandwidth. The dual-labeled probes including a reporter and a dark quencher are also called fluorogenic or turn-on probes, since a (bio-)chemical event causes their transition from a non-fluorescent to a (typically highly) fluorescent form.

Dabcyl (4-(4'-dimethylamino-phenylazo)benzoic acid) is a widely used dark quencher [1] in dual-labeled probes for a variety of biomolecular applications, like enzymatic catalysis and nucleic acid probes [2, 3].

Dabcyl is a molecule based on an azobenzene scaffold, which consists of two phenyl rings linked by an azo group (N=N) in which each nitrogen atom carries a non-bonding pair of electrons:

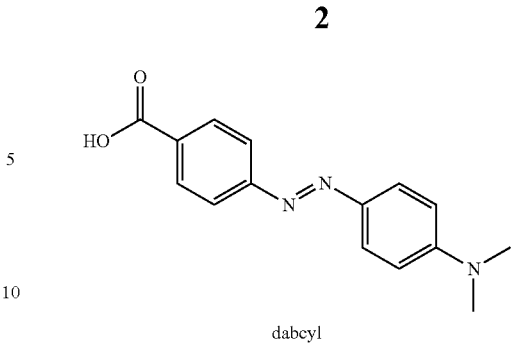

dabcyl

This aromatic system confers high hydrophobicity to dabcyl making it insoluble in aqueous solution. Therefore, stock solutions of dabcyl need to be prepared in DMSO.

The absorption band of dabcyl in the range of 400-550 nm overlaps with the emission band of many common fluorescent dyes such as EDANS (5-((2'-aminoethyl)amino)naphthalene-1-sulfonic acid; $\lambda_{em,\ Max}$=490 nm), monobromobimane (mBBr; $\lambda_{em,\ Max}$=480 nm), and many fluorescein, coumarin and rhodamine derivatives, e.g. carboxyfluorescein (FAM; $\lambda_{em}$=515 nm; in water), coumarine 1 ($\lambda_{em}$=448 nm; in ethanol), rhodamine 123 ($\lambda_{em}$=512 nm; in ethanol) to cite only a few.

Although dabcyl is one of the most popular acceptors for developing fluorescence resonance energy transfer-(FRET)-based biological probes, the very poor solubility in water set limits to its use in biological systems where the natural solvent is water. Although this hydrophobicity can be compensated by the hydrophilicity of the substrate to which dabcyl is linked (e.g. long DNA segments or peptide chains), it represents a real problem in case of comparatively small substrate (e.g. glutathione) in which this compensation is more difficult.

Solubility problems have been observed for several dabcyl-labeled substrates [4]. Incomplete dissolution leads to incorrect estimation of the concentrations and consequently wrong calculations of the stability and rate constants. Attempts to overcome the problems deriving from the insolubility have been done, e.g. by performing the enzymatic assays in mixture of water and DMSO [2].

Decreasing the hydrophobicity of a compound is usually done by adding either sulfonate or hydroxyl groups to the compound. The modification, however, must not lead to a change of the desired properties of the compound. In the case of dabcyl, it is imperative that the fluorescence properties, namely the function as dark quencher, are not changed. For example, the emitting properties of the compound must not be significantly affected by the modification. If the modification leads to a change of the emitting properties, the compound might become fluorescent itself and therefore is no longer suitable as a dark quencher. This effect is known to occur when hydroxyl groups are added to a compound. For example, the addition of one hydroxyl group transforms the weak fluorescence of phenylalanine in the red-shifted stronger fluorescence of tyrosine.

Furthermore, the modification must not lead to a significant change in the electrostatic profile of the compound, as its function is to interact with molecules in the context of biological systems, wherein the molecular interactions are often driven by electrostatics (e.g. enzymatic reactions). A change in the electrostatic profile is a known effect of the addition of sulfonate groups [5].

In addition, the modification must not lead to a significant structural change of the compound, which affects the interaction with molecules in the biological systems, where the compound is to be used. For example, it has to be prevented that catechols are formed by the modification, as the catechols strongly chelate metals (e.g. Fe(III)). The chelation leads to unwanted reactions that may interfere with the system under investigation. This aspect is particularly important for the investigation of enzymatic reactions in which metals are essential cofactors and for possible applications in vivo.

It was the problem to be solved by the present invention to provide a compound suitable as a dark quencher, which can be used in aqueous systems, is superior in spectroscopic properties compared to dark quenchers of the state of the art, and which is easier to handle.

This problem was solved by providing the compound 4-((4'-(dimethylamino)2',6'-dihydroxyphenyl)azo)2-hydroxybenzoic acid, which is herein also called Hydrodabcyl. Hydrodabcyl is easier to handle compared to dabcyl as it is soluble in aqueous solutions. It is superior to dabcyl as it has superior quenching abilities due to a higher molar absorbance compared to dabcyl.

A further problem to be solved by the present invention was to provide an improved method for synthesizing Hydrodabcyl. This problem is solved by providing the method as described.

SUMMARY OF THE INVENTION

A compound is provided, which acts as a dark quencher, and is water soluble. This compound is 4-((4'-(dimethylamino)2',6'-dihydroxyphenyl)azo)2-hydroxybenzoic acid, which is herein also called Hydrodabcyl.

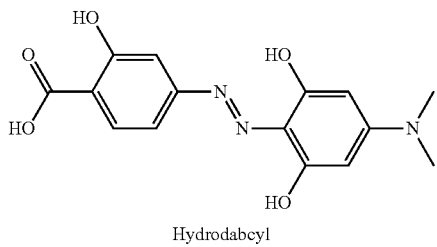 [SMILES: CN(C)c1cc(O)c(/N=N/c2ccc(C(=O)O)c(O)c2)c(O)c1]

Hydrodabcyl

Further provided is a method of producing the compound.

Details of the present invention are set forth in the accompanying drawings and the description below. Other features, objects, and advantages will be apparent from the description and the drawings.

DESCRIPTION OF DRAWINGS

FIGS. 6a and 6b show the ethidium bromide staining of DNA separated by agarose gel electrophoresis.

FIGS. 7a and 7b show the ethidium bromide staining of DNA separated by agarose gel electrophoresis.

FIG. 8a shows an oocyte injected with buffer. No fluorescence is detected.

FIG. 8b shows an oocyte injected with Substrate-Bim. Fluorescence is detected.

FIG. 8c shows an oocyte injected with Bim-Substrate-Hydrodabcyl. No fluorescence is detected, because Hydrodabcyl quenches the fluorescence of Substrate-Bim.

DETAILED DESCRIPTION OF INVENTION

A new compound is provided that is compatible with aqueous systems and thereby overcomes the problem of insolubility in aqueous solution and avoids the need for organic co-solvents, and at the same time has spectroscopic properties like dabcyl. The structure of the compound was designed and synthesized and it was found that a dimethylamino phenyl azobenzoic acid that is substituted with 3 hydroxyl groups at specific sites as indicated in the formula above is water-soluble and is surprisingly a superior dark quencher. The new compound—Hydrodabcyl or (4-((4'-(Dimethylamino)-2',6'-dihydroxyphenyl)azo)-2-hydroxybenzoic acid), thus, provides a very useful combination of properties.

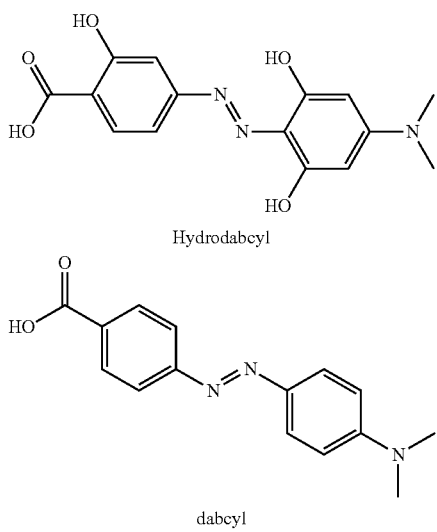

Hydrodabcyl dabcyl

The modification of the ring system with hydroxyl groups has the advantage that no charged groups are present, in contrast to the presence of sulfonate groups. Consequently, Hydrodabcyl will not significantly modify the electrostatic profile of the molecule to which it is linked and thus the binding properties of the labeled molecule are not altered. In addition, the position of the hydroxyl groups prevents the formation of catechols. Moreover, the choice of modifying the ring system has the practical advantage to keep the carboxyl group available for the coupling to an amino group in the substrate through a standard amide bond formation.

Figure 2:
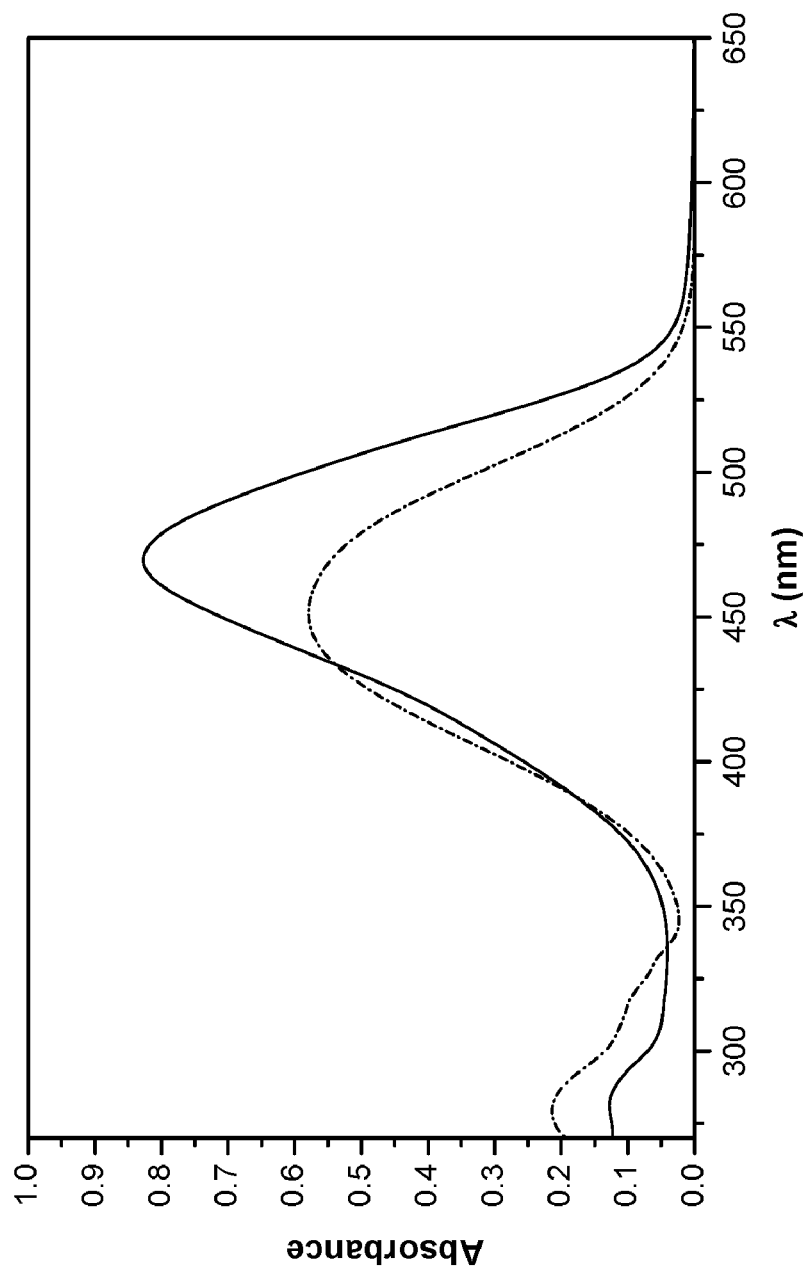
FIG. 2 shows a comparison of the absorption spectra of dabcyl (dash-dotted line, $\lambda_{max}$=451 nm) and Hydrodabcyl (solid line, $\lambda_{max}$=470 nm) at a concentration of $2\times10^{-5}$ M in DMSO at 20° C. The bathochromic shift (red-shift) of Hydrodabcyl can be observed.

Furthermore, although the new compound carries three hydroxyl groups in comparison to dabcyl, the emitting properties of the compound compared to those of dabcyl are not adversely affected. As shown in FIG. 2, the absorption spectra of dabcyl and Hydrodabcyl are similar. Thus, Hydrodabcyl is not only a water soluble alternative to dabcyl, but provides even better properties.

It was surprisingly found that by addition of the three hydroxyl groups at these specific locations, the molar absorbance and the width at half the peak height of Hydrodabcyl is increased compared to the molar absorbance and the width at half the peak height of dabcyl (see FIG. 2 and Example 2). A slight extension of the absorption band of Hydrodabcyl towards longer wavelength (bathochromic shift) compared to dabcyl is observed as well. The bathochromic shift together with its comparatively higher molar absorbance extends the quenching power of this new dark quencher compared to dabcyl. As it has been shown in FIG. 3, Hydrodabcyl has a higher molar absorbance in aqueous solution compared to DMSO. This property makes Hydrodabcyl an effective quencher for wavelengths up to 530 nm.

The changed absorbance properties alone make Hydrodabcyl a better dark quencher compared to dabcyl. The solubility in water crucially improves the value of Hydrodabcyl and makes it a superior dark quencher as it essentially improves the use of the compound in biological systems.

The solubility of Hydrodabcyl was tested at different pH values. At pH >7, solutions in the mM range can be directly prepared. At acidic pH (pH 4.5-7), the solubility is lower, however concentrations in the mM range can be nevertheless obtained by gradual acidification of the solution. It was found that Hydrodabcyl is soluble in aqueous solution in a mM concentration range at pH>7. At a pH of about 4.5 to 7, the solubility in a mM concentration range was confirmed by decreasing the pH-value of an alkaline solution (see Example 7 and FIGS. 9-11).

Figure 15:
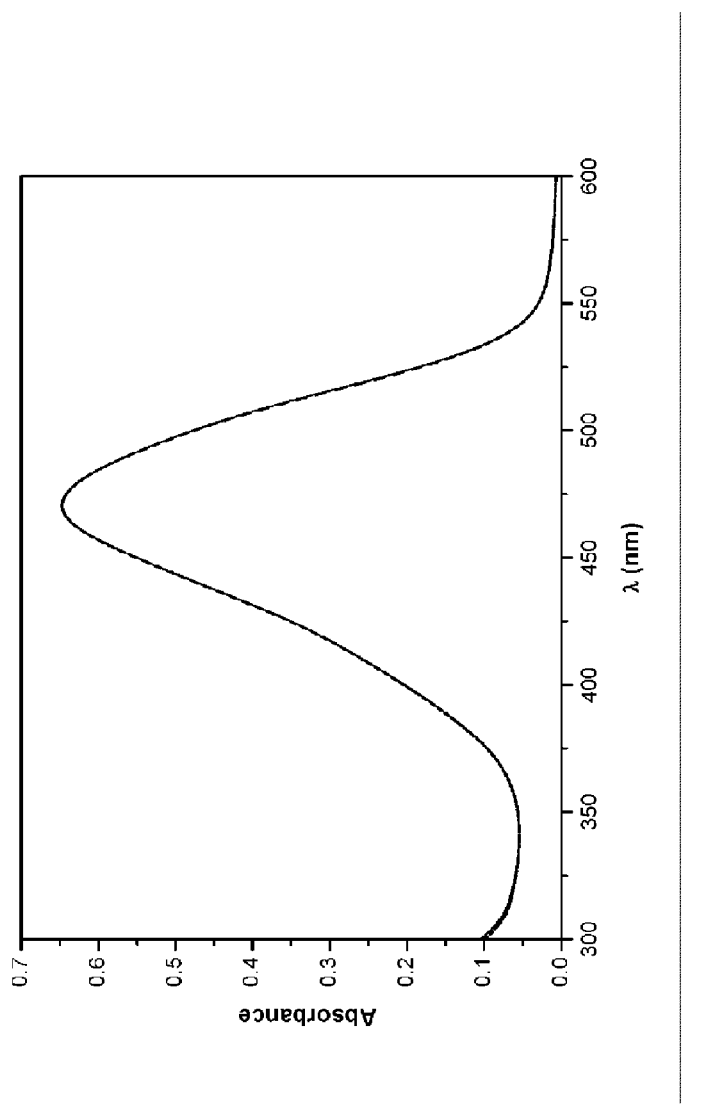
FIG. 15 shows the absorbance of Hydrodabcyl 17.5 μM in DMSO at 20° C. Spectrum recorded after the solution preparation in the dark (continuous line) and spectrum recorded after 5 min exposure to the light of a 60 W tungsten lamp (broken line). The two curves are indistinguishable.
Figure 16:
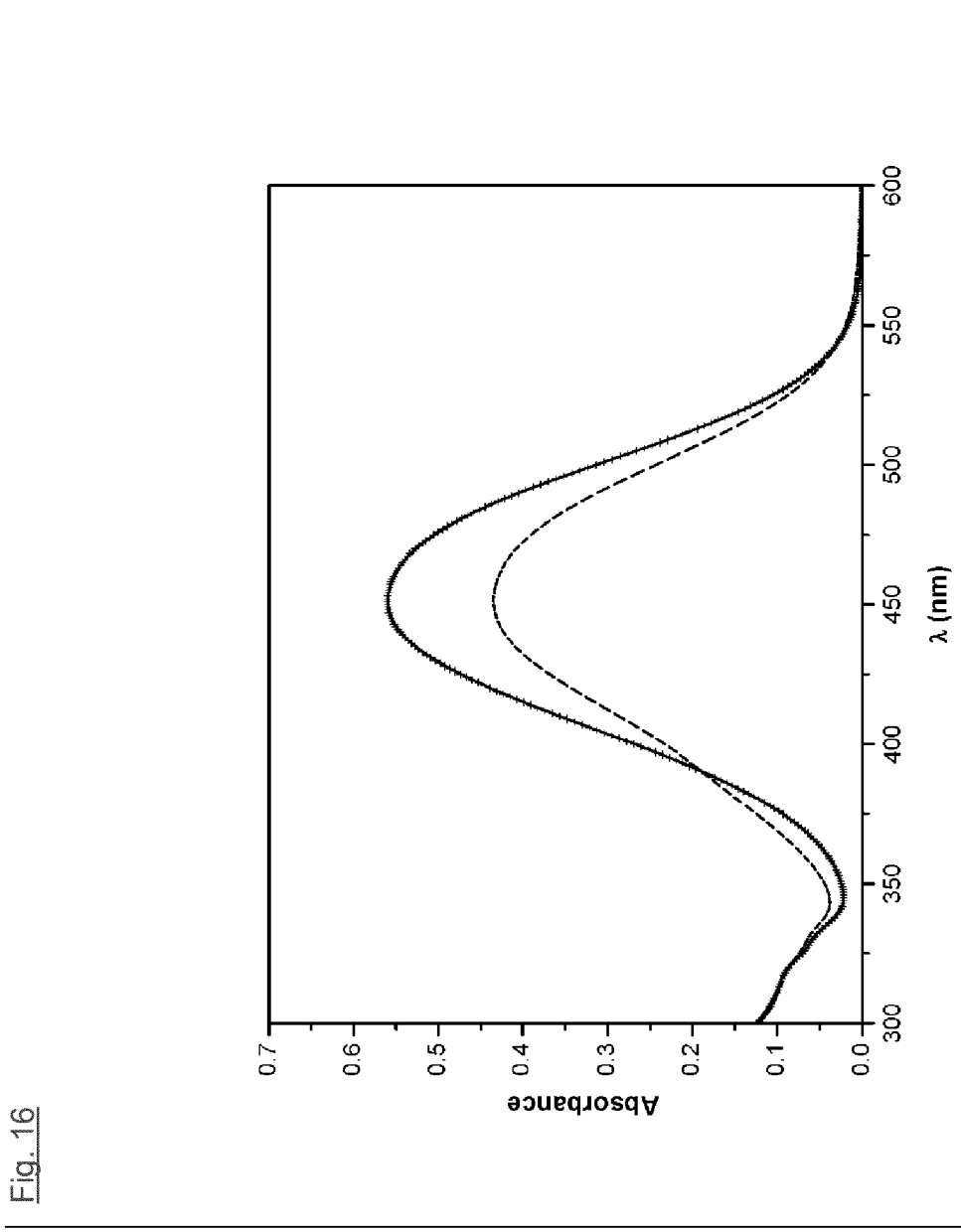
FIG. 16 shows the absorbance of dabcyl 17.5 μM in DMSO at 20° C. Spectrum recorded after the solution preparation in the dark (continuous line), spectrum recorded after 5 min exposure to the light of a 60 W tungsten lamp (broken line) and spectrum recorded after 10 min in the dark at 20° C. (crossed line). The continuous and crossed lines are indistinguishable.

Hydrodabcyl is also substantially easier to handle than dabcyl. In fact due to the water solubility, the aqueous solutions are easier to prepare, and glassware washing becomes easier. Moreover, Hydrodabcyl shows higher stability to light exposure in comparison to dabcyl (see Example 8 and FIGS. 15 and 16).

A further advantage of the compound of the present invention is that the solubility of Hydrodabcyl is achieved without changing the dimension of the chromophore appreciably. A small chromophore has the advantage to minimize the sterical hindrances introduced in the molecular system by the labelling process. Ideally, a labelling chromophore should not affect the molecular system to investigate at all; in practice, the influence of the labelling chromophore, which is often unavoidable, has to be minimized. Therefore the comparatively small dimension of Hydrodabcyl is a crucial feature that, together with the absence of charged groups, makes it an excellent chromophore, especially in the case of small substrate.

Hydrodabcyl is also suitable to be used in biological systems as it has been determined that Hydrodabcyl is neither carcinogenic (see Example 3), nor cytotoxic (see Examples 3 and 4), or teratoxic (see Example 6). It was further shown that Hydrodabcyl is functional in vivo, as it effectively quenches the fluorescence of a fluorescent substrate in vivo (see Example 5).

A compound suitable for use as a component of a fluorogenic probe in biological systems has to be stable and is preferably in purified form. Therefore, a further aspect of the present invention is a method for producing Hydrodabcyl in stable and pure form. It has been found that Hydrodabcyl can be synthesized and obtained as non-fluorescent compound that is useful as dark quencher by using the method as claimed in claim 2.

According to the method of the present invention, a compound having formula (I)

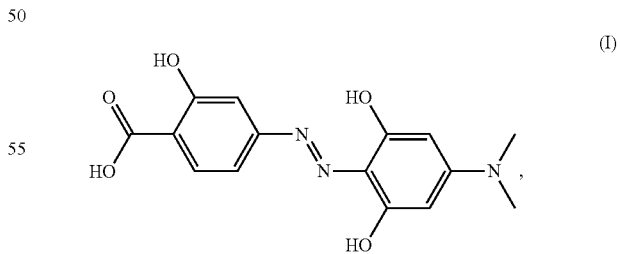

(I)

is produced wherein the method comprises the steps of
a) producing 5-dimethylamino-resorcinol (5-(dimethylamino)benzene-1,3-diol) by reacting phloroglucinol (benzene-1,3,5-triol) with dimethylamine ($HN(CH_3)_2$) to obtain 5-dimethylamino-resorcinol;
b) azo-coupling 4-diazo-salicylic acid to 5-dimethylamino-resorcinol to obtain the compound having formula (I).

4-diazo-salicylic acid can be obtained by reacting 4-aminosalicylic acid with $NaNO_2$ and HCl.

Figure 1:
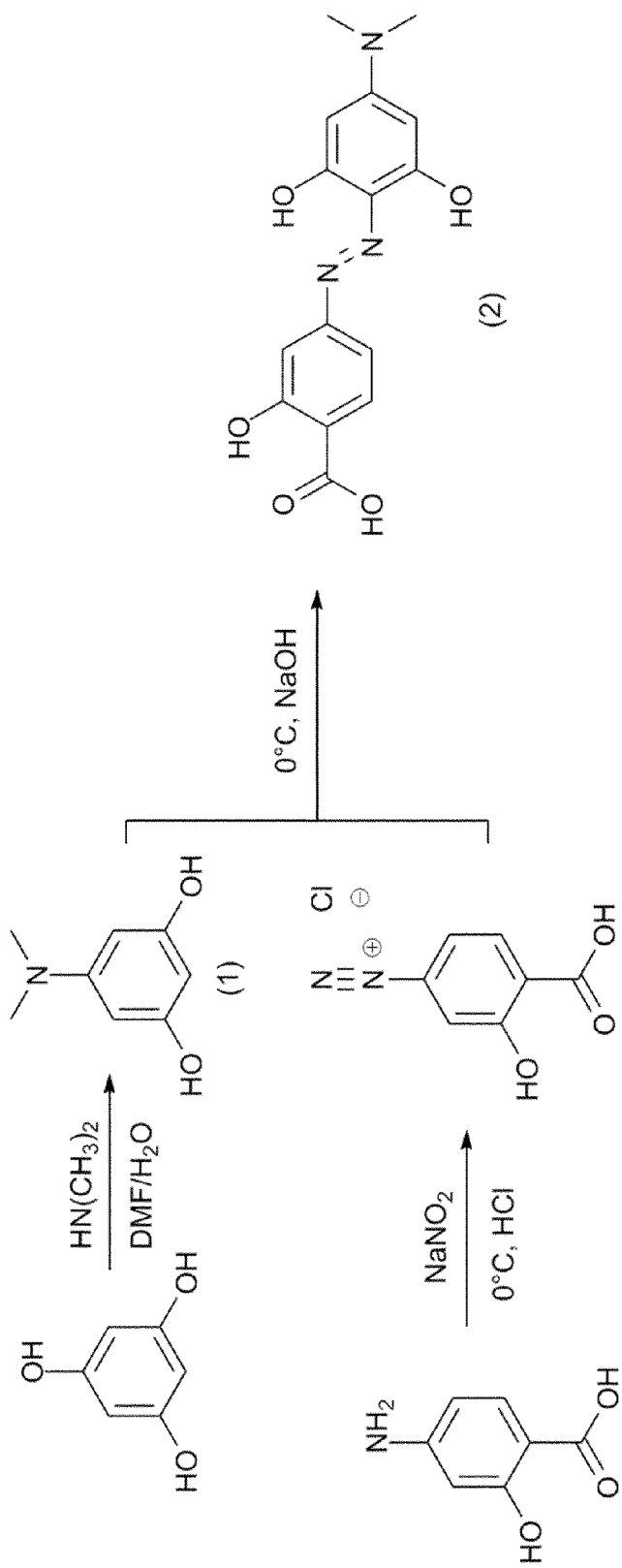
FIG. 1 shows the scheme of the synthesis of 4-((4'-(dimethylamino)2',6'-dihydroxyphenyl)azo)2-hydroxybenzoic acid (Hydrodabcyl). 5-dimethylamino-resorcinol (1) is produced and azo-coupled to a diazotized 4-aminosalicylic acid to synthesize 4-((4'-(dimethylamino)2',6'-dihydroxyphenyl)azo)2-hydroxybenzoic acid (2).

Thus, Hydrodabcyl can be synthesized in two steps (see also FIG. 1 and Example 1). The first step in the chemical synthesis consists in exchanging one —OH group of phloroglucinol with a dimethylamino group and isolating the intermediate product (see FIG. 1 and Example 1), in a second step 4-diazo salicylic acid and 5-dimethylamino-resorcinol are reacted to yield the compound of the present invention.

It was found that the synthesis of 5-dimethylamino-resorcinol as disclosed by Petrzilka [6] did not result in a useful product. The crystals of 5-dimethylamino-resorcinol appeared pink as reported in the work of Petrzilka. If these crystals were used in the second step, the final product, i.e. the compound obtained by reaction of 5-dimethylamino-resorcinol with diazotized 4-aminosalicylic acid to obtain Hydrodabcyl, was fluorescent and, thus, could not be used as dark quencher. Furthermore, it was observed that the solution of 5-dimethylamino-resorcinol prepared according to the method of [6] became intensely colored after being stored for some days. A new method of producing a purified 5-dimethylamino-resorcinol was therefore needed.

It was surprisingly found that the fluorescence and the coloring of the final product can be avoided by purifying the intermediate product 5-dimethylamino-resorcinol before using it in the second step. It is assumed that the undesirable fluorescence is caused by an impurity.

It was found that by performing a purification step based on column chromatography, preferably using silica gel, a stably colorless solution can be obtained.

Therefore, the method of producing the compound having formula (I) can comprise a further step a1) wherein the compound obtained in step a) is purified by (i) concentrating the 5-dimethylamino-resorcinol; (ii) purifying the residue obtained in step (i) by column chromatography; and (iii) crystallizing the purified compound obtained in step (ii).

This improvement to the method of the prior art by adding the above mentioned purification process leads to a non-fluorescent final product, which can be used as dark quencher. The method of the present invention provides Hydrodabcyl efficiently and in high quality. An overall yield of about 60% or more can be obtained. A process for the preparation of Hydrodabcyl is described in detail in Example 1.

Briefly, the method of the present invention comprises the following steps.

In a first step 5-dimethylamino-resorcinol is prepared by reacting phloroglucinol and dimethylamine hydrochloride. In one embodiment of the method, phloroglucinol is dissolved in a mixture of dimethylformamide and water, preferably degassed, under argon. Dimethylamine hydrochloride is added. Subsequently in the course of the reaction, which can take some hours, for example about 4-6 hours, a base, such as NaOH is added to adjust the pH. The addition of dimethylamine hydrochloride and base can be repeated several times. The resulting dark solution comprises the desired intermediate product 5-dimethylamino-resorcinol. The intermediate product is isolated and purified to remove undesirable impurities. In one embodiment the intermediate product is concentrated in vacuo and the residue is purified by column chromatography on a silica gel. Purified 5-dimethylamino-resorcinol can be crystallised from dichloromethane as white crystals. These crystals can be used directly for the next step without storage.

The second step consists of azo-coupling 5-dimethylamino-resorcinol and 4-diazo-salicylic acid to get the final product 4-((4'-(dimethylamino)-2',6'-dihydroxyphenyl)azo)-2-hydroxybenzoic acid. 4-diazo-salicylic acid can be prepared by adding a solution of $NaNO_2$ to a solution of 4-aminosalicylic acid. The reaction can be carried out by heating. Finally the end product can be isolated by dissolving the desired product in a solvent, for example in methanol, filtering off impurities, and removing the solvent, such as by evaporation.

The obtained product can be further purified, for example as follows. The sediment can be diluted in a base, for example NaOH, and then filtered. An acid, for example formic acid, for acidification and a solvent, for example ethanol, are then added to the filtrate and the mixture is cooled, for example, in a fridge. After one or more centrifugation and resuspension steps, the residue is dispersed in distillate water by ultrasonic bath and then frozen, for example in liquid nitrogen and dried, for example by lyophilisation.

The purification of the product can be further optimized through its precipitation at pH<4 and centrifugation. Therefore, the method of producing the compound having formula (I) can further comprise a step b1), wherein the compound obtained in step b) is purified by precipitation at pH<4 followed by centrifugation.

In conclusion, Hydrodabcyl is a novel dark quencher, based on an azobenzene-scaffold, with an optimal solubility in aqueous solution. Its small dimension, the absence of charged groups and its absorption range make Hydrodabcyl the dark quencher of choice in tandem with many commercially available fluorescence donors. The novel dark quencher Hydrodabcyl represents an improved alternative to the very popular dabcyl in the design of fluorogenic probes.

EXAMPLES

Preferred embodiments of the invention are outlined in the following examples which should not be interpreted as restricting the scope or spirit of the invention.

The chemicals used were purchased from commercial sources and used without further purification, unless indicated otherwise. DMSO was obtained from Sigma. The typical aqueous solution consisted in 50 mM sodium phosphate buffer pH=8.0.

The following apparatuses and methods were used.

The reaction progress was monitored by Thin Layer Chromatography (TLC) on pre-coated silica plates (Merck TLC Silica gel 60 F254) and the spots were visualized by UV light and stained with ceric ammonium molybdate.

Chromatography was carried out using Macherey-Nagel 60 silica gel (230-400 mesh).

The $^1H$ and $^{13}C$ NMR spectra were taken on a Bruker Avance 300 MHz spectrometer.

Chemical shifts are reported in parts per million (ppm) referenced with respect to residual solvent ($CDCl_3$=7.26 ppm, $D_2O$=4.49 ppm).

IR spectra were recorded with a FT-IR spectrometer PerkinElmer S100 equipped with an Attenuated Total Reflection (ATR) unit.

High Performance Liquid Chromatography (HPLC) was performed on Phenomenex RP Kinetex 5 um C18 100 Å, 250×4.6 mm (analytical) column. 0.1% $HCOOH/H_2O$ and MeOH were used as eluents for HPLC experiments with flow rate of 0.7 ml/min.

Double beam Perkin Elmer Lambda 750 UV/Vis spectrophotometer equipped with a thermostated cuvette holder was used to record the absorption spectra over a wavelength range 200-800 nm at 20° C.

Example 1: Synthesis of Hydrodabcyl

The compound 4-((4'-(dimethylamino)-2',6'-dihydroxyphenyl)azo)-2-hydroxybenzoic acid (Hydrodabcyl) was synthesized in two steps as outlined in the scheme shown in FIG. 1.

The first step consists in the production of 5-dimethylamino-resorcinol (1), based on the method of (Petrzilka [6]), which has been further developed and improved to allow to obtain Hydrodabcal in the desired quality. The method comprises a purification step over silica gel following the completion of the reaction. The purification step yields colourless crystals, whereas the crystals obtained by the method described previously yielded pink crystals [6]. The reported pink color is most probably caused by contaminations by a degradation product. This assumption is supported by the observation that the product turns pink when it is stored for several weeks in the refrigerator. This contamination leads in the next step to an undesired fluorescent product (in addition to the desired Hydrodabcyl), which cannot be separated even by HPLC. In contrast thereto, the method of the present invention avoids the formation of this by-product.

5-Dimethylamino-resorcinol (1)

phloroglucinol (9.23 g, 73.2 mmol) was dissolved in a degassed mixture of dimethylformamide (128 ml) and water (95 ml) under argon. Then dimethylamine hydrochloride (8 g, 91.5 mmol) was added. Subsequently over a time period of 5 hours one pellet of NaOH after another was added (whole amount 3.66 g, 91.5 mmol). The mixture was stirred overnight at room temperature. During the next 48 hours dimethylamine hydrochloride and NaOH were added 3 times (every time 10% of first addition). Then the dark solution was concentrated in vacuo and the residue was purified by column chromatography (silica gel 60; cyclohexane/ethyl acetate 1:1, $R_f$ 0.38). The product was crystallised from dichloromethane with yield: 8.2 g (73%) as white crystals of m.p. 151° C. and used directly for the next step without storage.

IR (ATR): 3276, 2972, 2884, 2512, 1604, 1512, 1462, 1435, 1377, 1347, 1312, 1276, 1247, 1128, 1042, 1005, 987, 853, 831, 809, 686, 634, 576 cm-1; $^1$H NMR (300 MHz, DMSO-$d_6$) δ ppm 2.78 (s, 6H), 5.61 (s, 3H), 8.82 (s, 2H); $^{13}$C NMR (75 MHz, DMSO-$d_6$) δ 158.8, 152.3, 92.0, 91.5, 40.1 ppm.

The second step consists of modified azo-coupling to get the final product 4-((4'-(dimethylamino)2',6'-dihydroxyphenyl)azo)2-hydroxybenzoic acid (2) with overall yield 58% after 2 steps [7]. The purification of the product is optimized through its precipitation at pH<4 and centrifugation.

4-((4'-(Dimethylamino)-2',6'-dihydroxyphenyl)azo)-2-hydroxybenzoic acid (2)

A cooled freshly prepared solution of 2.5 M NaNO$_2$ (9 ml, 22.5 mmol) was added dropwise to a cooled solution of 4-aminosalicylic acid (3.46 g, 22.5 mmol) in a half concentrated HCl (6 ml) at 0-5° C. The solution was then stirred for another 15 min and introduced dropwise at 0-5° C. to 5-dimethylamino-resorcinol (3.45 g, 22.5 mmol) in 1M NaOH (23.5 ml). The mixture was heated at 70° C. for 15 min and then stirred for 1 h at room temperature. Methanol was added to the red mixture and the mixture was then put in an ultrasonic bath for several minutes.

The impurities were filtered and the filtrate was evaporated. The sediment was diluted in 0.1N NaOH and then filtered. Formic acid for acidification and ethanol were added to the filtrate and the mixture was placed into the fridge for 15 h. Then the mixture was centrifuged at −4° C., and the pellet was suspended in 0.1% formic acid and centrifuged again. This procedure was repeated 3 times. Afterwards the residue was resuspended in bi-distillate water and centrifuged twice. Finally, the substance was dispersed in bi-distillate water by ultrasonic bath and then frozen in liquid nitrogen and dried by lyophilisation.

Pure final product (2) was obtained with yield: 5.7 g (80%) as red powder of m.p. 253° C. and stored in the darkness in the fridge at 4-8° C.

HPLC: T=16.5 min (MeOH— 0.1% HCOOH/H$_2$O 55-45, $\lambda_{max}$=455 nm); IR (ATR): 3352, 3083, 2908, 2737, 2475, 1874, 1656, 1620, 1502, 1473, 1426, 1387, 1337, 1291, 1226, 1191, 1133, 1087, 1018, 983, 965, 886, 847, 811, 776, 729, 675 cm-1; $^1$H NMR (300 MHz, DMSO-$d_6$) δ 3.07 (s, 6H), 5.73 (s, 2H), 7.12 (dd, J=8.2, 1.9 Hz, 1H), 7.29 (d, J=1.9 Hz, 2H), 7.78 (d, J=8.5 Hz, 2H) ppm; $^{13}$C NMR (75 MHz, DMSO-$d_6$) δ 172.1, 163.3, 158.2, 152.0, 131.7, 124.9, 113.6, 110.19, 105.6, 91.9, 40.4 ppm; ESI-MS: 316.0925 [M−H]$^-$, 317.0982[M] and 318.1001 [M+H]$^+$. HRMS calc. 317.1012 for $C_{15}H_{15}N_3O_5$, found 317.0982.

Example 2: Comparison of Absorption Spectra of Dabcyl and Hydrodabcyl

The absorption spectra of Hydrodabcyl and dabcyl were compared (see FIG. 2). Dabcyl has a $\lambda_{max}$=451 nm, whereas Hydrodabcyl has a $\lambda_{max}$=470 nm at a concentration of 2×10$^{-5}$ M in DMSO at 20° C. The molar absorbance and the width at half the peak height of Hydrodabcyl is increased compared to the molar absorbance and the width at half the peak height of dabcyl. The bathochromic shift (red-shift) of Hydrodabcyl can be observed.

Figure 3:
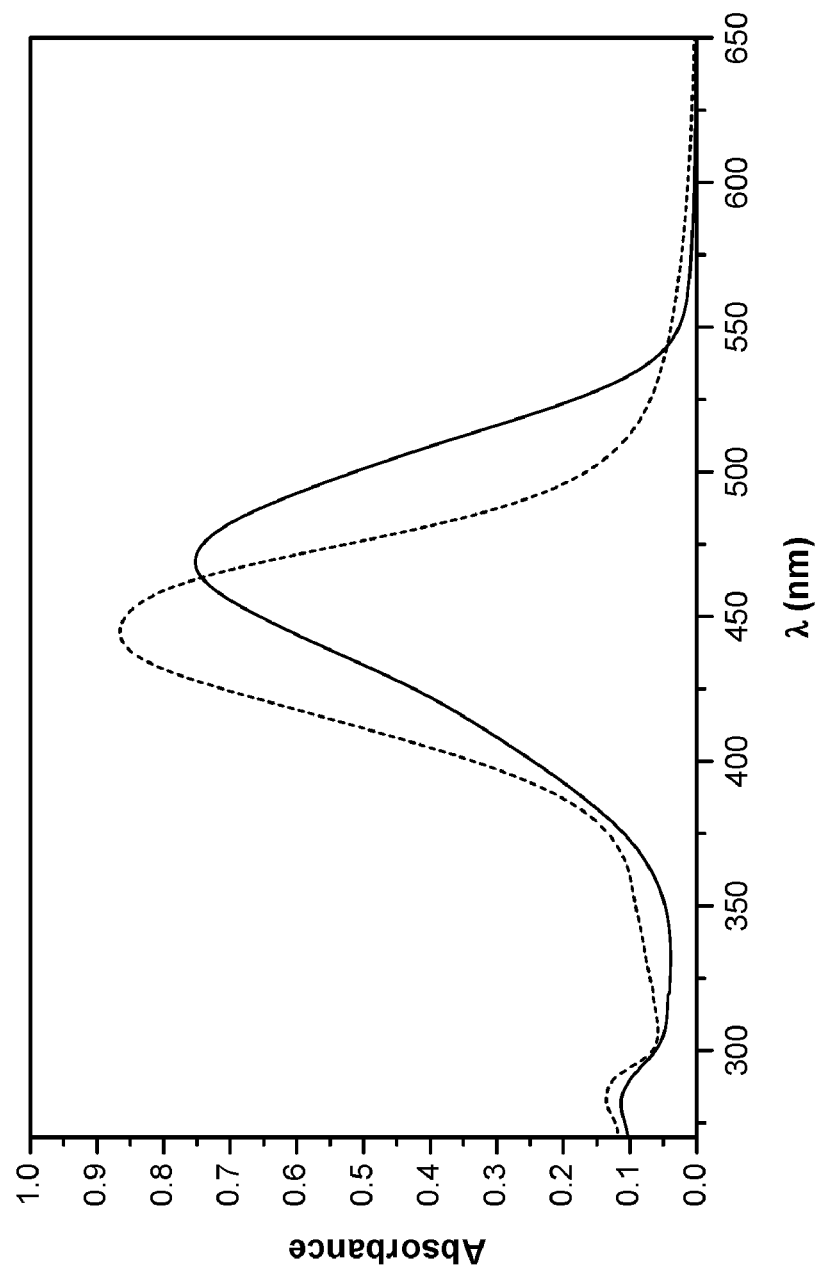
FIG. 3 shows a comparison of the absorption spectra of Hydrodabcyl (concentration: $2\times10^{-5}$ M; temperature 20° C.) in DMSO (solid line, $\lambda_{max}$=470 nm, $\epsilon$=37000±1000 L·mol$^{-1}$·cm$^{-1}$) and in 50 mM sodium phosphate buffer pH=8.0 (dotted line, $\lambda_{max}$=445 nm, $\epsilon$=43000±1000 L·mol$^{-1}$·cm$^{-1}$). The hypsochromic shift (blue-shift) in the buffer can be observed.
Figure 4:
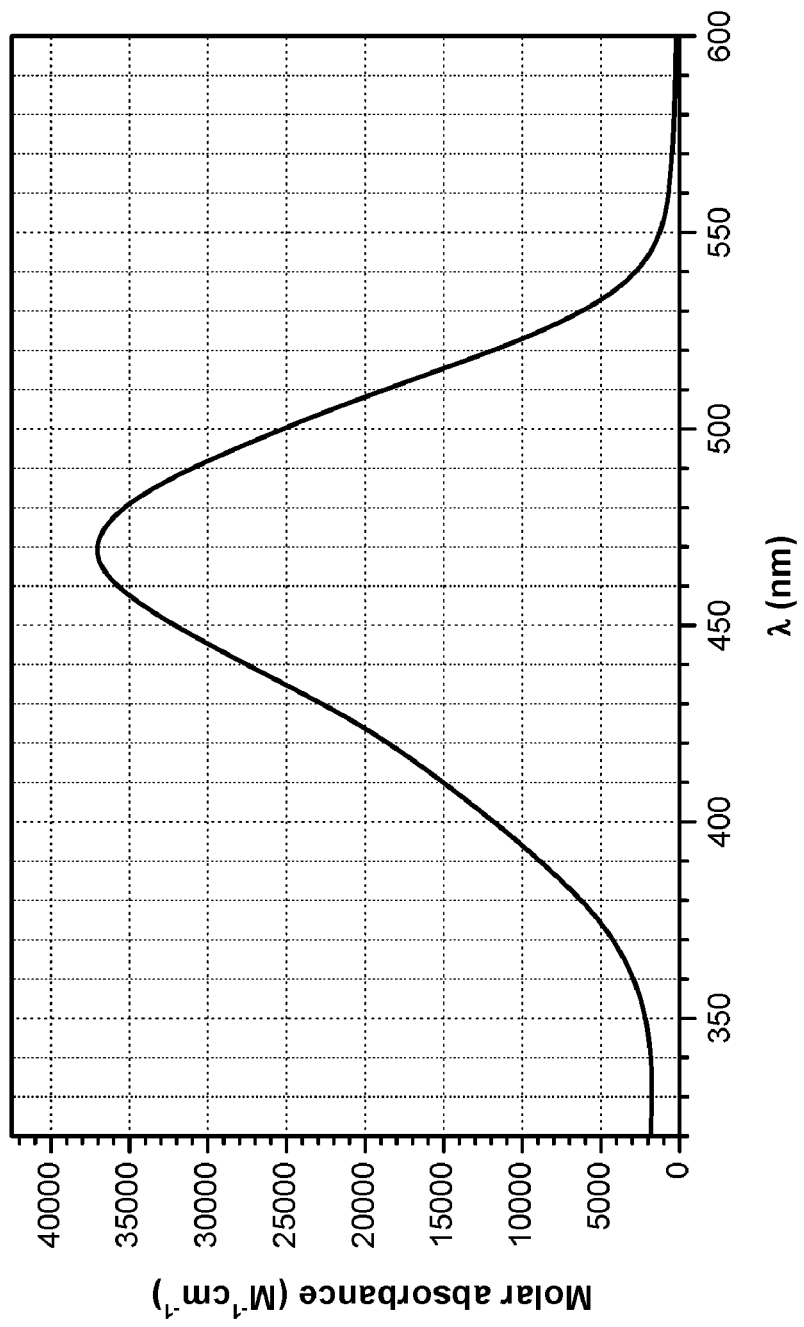
FIG. 4 shows the molar absorbance of Hydrodabcyl in DMSO.
Figure 5:
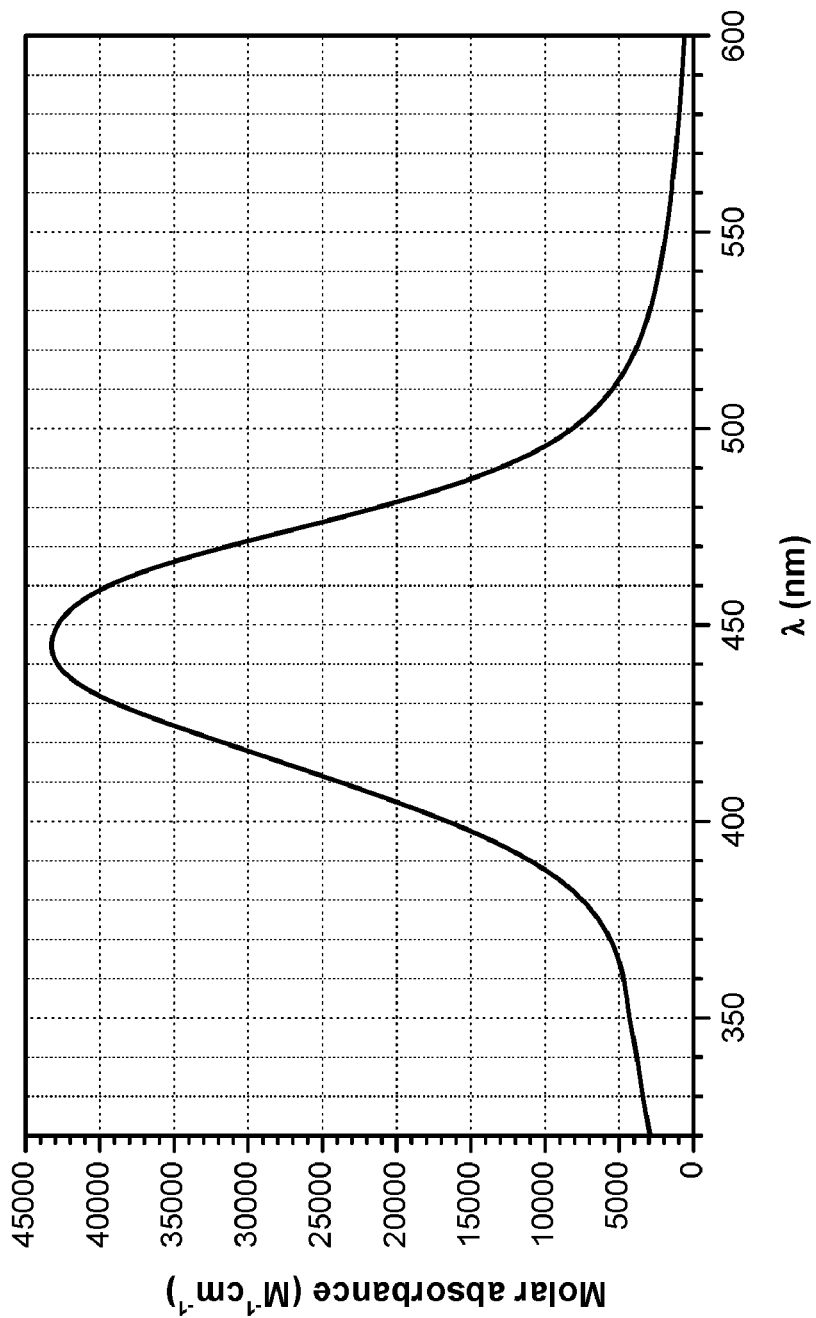
FIG. 5 shows the molar absorbance of Hydrodabcyl in 50 mM sodium phosphate buffer at pH=8.0.

The absorption spectrum of Hydrodabcyl in aqueous solution ($\lambda_{Max}$=445 nm, $\epsilon_{445}$=43000 M$^{-1}$ cm$^{-1}$) shows a hypsochromic shift in comparison to its spectrum in DMSO ($\lambda_{Max}$=470 nm, $\epsilon_{470}$=37000 M$^{-1}$ cm$^{-1}$) as shown in FIG. 3.

Example 3: Electrophoretic Mobility Shift Assay (EMSA)

In order to prove in vivo suitability of Hydrodabcyl, an Electrophoretic Mobility Shift Assay (EMSA) was carried out.

Figure 6:
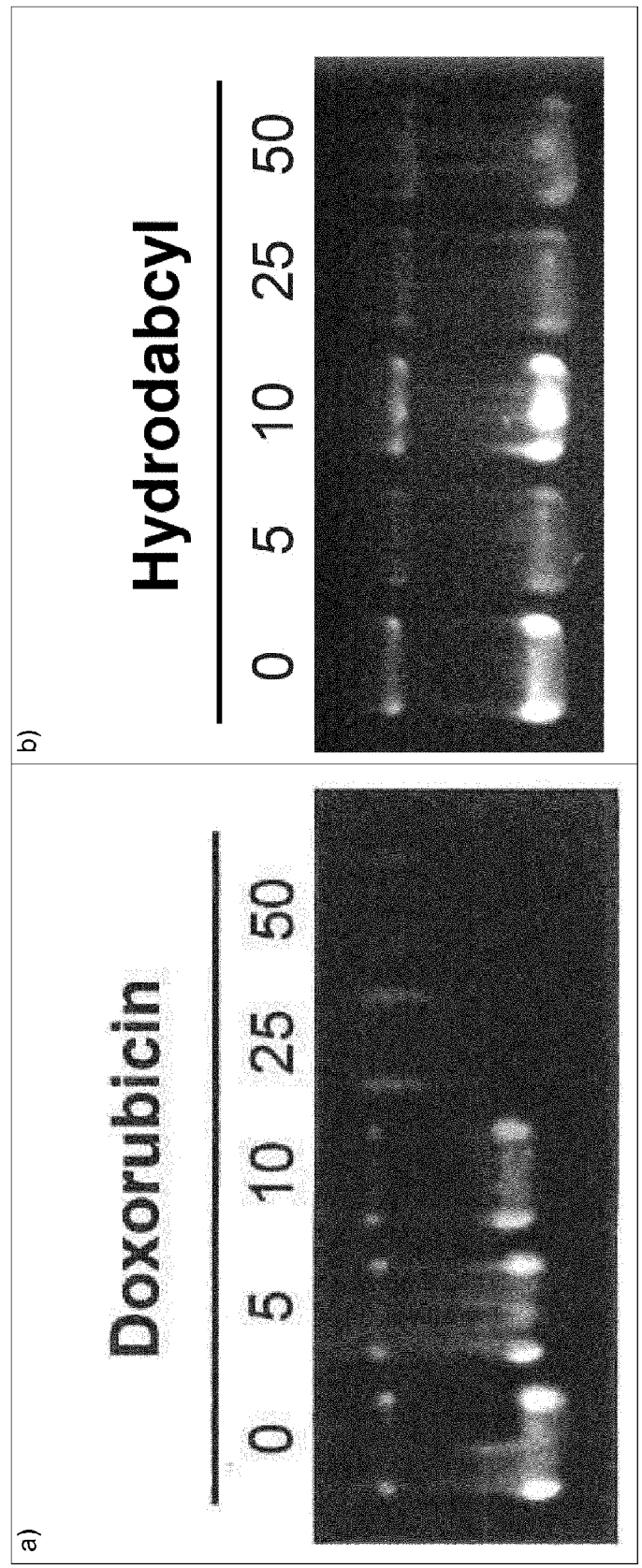
FIG. 6 shows the result of the Electrophoretic Mobility Shift Assay (EMSA) carried out with circular double-stranded DNA pBR322. The DNA was incubated for 24 hours with various concentrations (0, 5, 10, 25, 50 μM) of (a) doxorubicin and (b) Hydrodabcyl.
Figure 7:
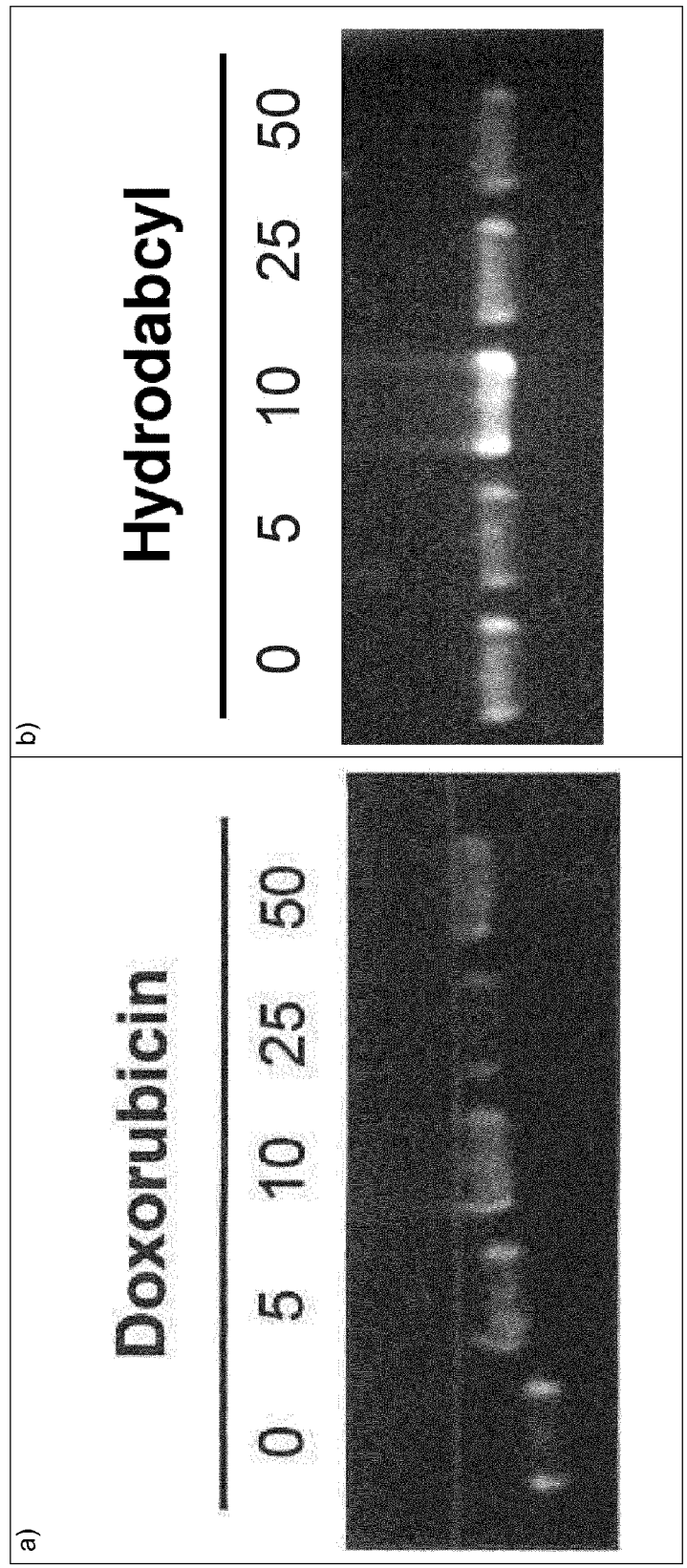
FIG. 7 shows the result of the Electrophoretic Mobility Shift Assay (EMSA) carried out with linear double-stranded DNA pBR322. The DNA was incubated for 24 hours with various concentrations (0, 5, 10, 25, 50 μM) of (a) doxorubicin and (b) Hydrodabcyl.

Circular and linear double-stranded DNA was incubated with various concentrations of Hydrodabcyl and doxorubicin (a known intercalating substance). After 24 h of incubation time, agarose gel electrophoresis was carried out. The results are shown in FIGS. 6 and 7.

The intercalation of doxorubicin into the DNA results in a shift of the DNA bands with increasing doxorubicin concentration, as can be seen in FIGS. 6a and 7a, where the results of the incubation of the DNA with doxorubicin are shown. The shifting of the bands shows the changes in mobility of the DNA in the agarose gel due to the structural changes in the DNA due to intercalation of doxorubicin into the DNA. The absence of the shift when incubated with Hydrodabcyl shows that Hydrodabcyl does not intercalate or bind to the DNA, presumably due to the decreased lipophilicity of Hydrodabcyl. Since intercalation is an important indication of toxicity (in particular carcinogenicity), this finding is an indication that Hydrodabcyl is not toxic.

Example 4: Cytotoxicity

To further prove in vivo suitability of Hydrodabcyl, a cytotoxicity assay was carried out as well.

Three different cell culture types were incubated with various concentrations (from 5 to 100 μM) of Hydrodabcyl.

Table 1 below shows the inhibitory concentration ($IC_{50}$) after incubation for 72 hours.

TABLE 1

| Cell culture type | $IC_{50}$ [μM] |
|---|---|
| HT-29 | >50 |
| EaHy.926 | >50 |
| CHF | >100 |

This test shows that Hydrodabcyl is not cytotoxic.

Example 5: In Vivo Fluorescence

Figure 8:
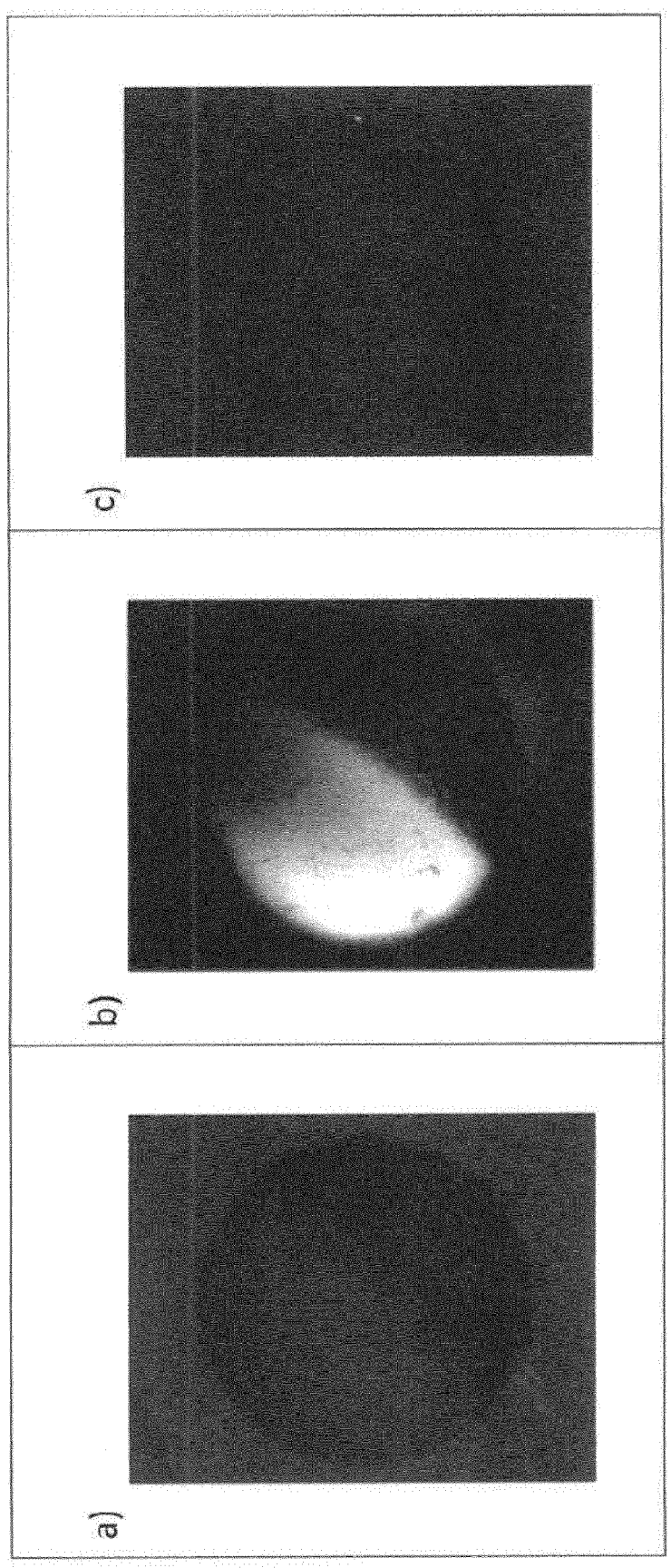
FIG. 8 shows the results of the in vivo fluorescence assay.

Two sorts of labelled molecules were injected into oocytes of *Xenopus laevis*:
A molecule labelled with monobromobimane (mBBr; a fluorescent dye, which emits light in the absorption spectrum of Hydrodabcyl); the molecule is called Substrate-Bim
A molecule labelled with mBBr and Hydrodabcyl (a fluorescence quencher); the molecule is called Bim-Substrate-Hydrodabcyl
As negative control oocytes were injected with buffer.
FIG. 8 shows the results of the in vivo fluorescence assay.
FIG. 8*a* shows an oocyte injected with buffer. No fluorescence is detected.
FIG. 8*b* shows an oocyte injected with Substrate-Bim. Fluorescence is detected.
FIG. 8*c* shows an oocyte injected with Bim-Substrate-Hydrodabcyl. No fluorescence is detected, because Hydrodabcyl quenches the fluorescence of Substrate-Bim. This assay proves that Hydrodabcyl is an effective fluorescence quencher in vivo.

Example 6: Influence of Hydrodabcyl on Embryogenesis

The effect on embryogenesis of the molecules injected into the oocytes as described in Example 5 was observed. The results are shown in Table 2 below.

TABLE 2

| Injected molecule | Living embryos after 24 h (%) |
|---|---|
| Only Buffer | 65 |
| Substrate-Bim | 61 |
| Bim-Substrate-Hydrodabcyl | 71 |

The similarity between the percentages shows that Hydrodabcyl does not influence embryogenesis.

Example 7: Quantitative Determination of the Solubility of Hydrodabcyl (in Comparison to the Parent Molecule Dabcyl)

In order to prove the superiority of hydrodabcyl, the solubilities of hydrodabcyl and dabcyl in pure water and buffered aqueous solutions were measured and compared.

Figure 9:
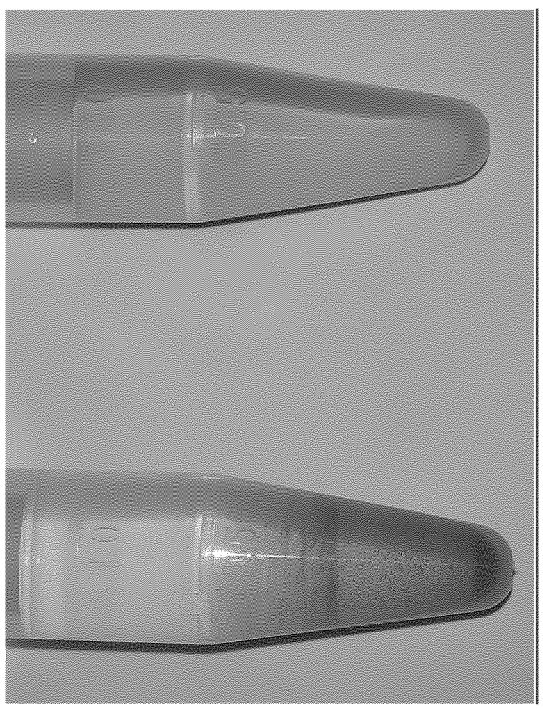
FIG. 9 shows evidence of precipitation of dabcyl in water (tentative concentration of about 7 μM (on the left); and a clear solution of Hydrodabcyl in water (7 μM) on the right.

Hydrodabcyl is soluble in water, in contrast to dabcyl. A limiting concentration of $5.71 \times 10^{-4}$ M for Hydrodabcyl in water was measured at 20° C. It was not possible to obtain a saturated solution of dabcyl due to precipitation. Evidence of precipitation of dabcyl in water (tentative concentration of about 7 μM) is shown in FIG. 9 on the left. On the right in FIG. 9, a clear solution of Hydrodabcyl in water (7 μM) can be seen.

In order to increase the solubility, the same tests were performed in a buffered aqueous solution at pH 8. As expected, the concentration of a saturated solution of Hydrodabcyl was much higher (25 mM). In a buffered solution pH 8 dabcyl is also soluble, although poorly; in fact a saturated solution of dabcyl has a concentration of orders of magnitude lower than a saturated solution of Hydrodabcyl, confirming the superiority of Hydrodabcyl.

The excellent solubility of the bare chromophore in aqueous solution already confers to Hydrodabcyl several practical advantages, e.g., aqueous solutions of Hydrodabcyl are easier to prepare and glassware can be more readily cleansed. Nevertheless, in most of applications the chromophores are linked to the molecules of interest. For example, to monitor protease activity chromophores are usually linked to the peptidic substrate. Both dabcyl and Hydrodabcyl can be easily coupled to an amino group through a standard amide bond formation. This reaction, however, eliminates the charge of the carboxylate that proved to contribute to the solubility of the bare chromophores at basic pH, with the risk to lead to insolubility. To investigate the behavior of dabcyl and Hydrodabcyl coupled to an amino acid bearing an amino group, dabcyl and Hydrodabcyl were linked to the amino group of a Lys side chain, and the solubility of the Lys-dabcyl and Lys-Hydrodabcyl moieties in a buffered aqueous solution at pH 8 were tested.

Interestingly, the concentration of the saturated solution of Lys-dabcyl was only $7.6 \times 10^{-6}$ M, whereas with Lys-Hydrodabcyl a 6.6 mM solution could be prepared without reaching saturation. This data indicates that the solubility of Lys-Hydrodabcyl is much higher than 6.6 mM and closer to the solubility of L-Lys which is reported to be 5.8 g per 1 kg of water, corresponding to about 40 mM [8].

These results indicate that Hydrodabcyl has minimal effect on the solubility of the peptidic substrate, whereas the hydrophobicity of dabcyl drastically affects the solubility of natural substrates in aqueous solution. A strongly reduced solubility of the products of an enzymatic reaction may hinder their release from the active site resulting in an inhibiting effect, which distorts the catalytic mechanism, thus preventing its understanding. These tests emphasize the superiority of Hydrodabcyl in biochemical applications.

Table 3. Summary of the results of the solubility tests (NaP buffer=sodium-phosphate buffer)

TABLE 3

Summary of the results of the solubility tests
(NaP buffer = sodium-phosphate buffer)

| Solvent | Substance | Solubility | Comments |
|---|---|---|---|
| Water, 20° C. | Hydrodabcyl | $5.71 \times 10^{-4}$ M | pH = 4.5 |
| | dabcyl | n.d. | not determined due to precipitation |
| 50 mM NaP buffer, pH 8.0 | Hydrodabcyl | $2.54 \times 10^{-2}$ M | |
| | dabcyl | $5.41 \times 10^{-4}$ M | |

TABLE 3-continued

Summary of the results of the solubility tests
(NaP buffer = sodium-phosphate buffer)

| Solvent | Substance | Solubility | Comments |
|---|---|---|---|
| 50 mM NaP buffer, pH 8.0 | Lys-Hydrodabcyl | >6.61 × 10$^{-3}$ M | The solution was not saturated |
| | Lys-dabcyl | 7.62 × 10$^{-6}$ M | |

Hydrodabcyl is very well soluble in aqueous solution over the whole biologically relevant pH range. From basic pH down to pH 6, solutions with concentrations in the millimolar range can be prepared directly at the desired pH. Although at pH<6 the solubility is lower, as the solubility test in pure water showed, solutions with mM concentrations can still be prepared by gradual acidification of an alkaline solution down to a pH value of 4.3.

Description of the Experiment:

Buffered solutions (50 mM sodium phosphate) have been prepared at four different pH: 8.0, 7.0, 6.0 and 5.5, respectively. The amount of Hydrodabcyl required to reach a concentration of 5 mM was immersed in each buffer solution and kept for 1 h at 30° C. in an ultrasonic bath. Clear solutions of Hydrodabcyl have been obtained at pH 8.0, 7.0 and at pH 6.0, whereas at pH 5.5 the substance was not completely soluble. To confirm its solubility, the absorbance of Hydrodabcyl was monitored as function of its concentration. Since the stock solution was too concentrated to be measured directly, three diluted solutions with different concentrations (10 μM, 20 μM and 30 μM) were prepared from each stock solution at pH 8.0, pH 7.0 and pH 6.0. The aliquots have been taken from different part of the volume of the stock solution to test the homogeneity.

Figure 10:
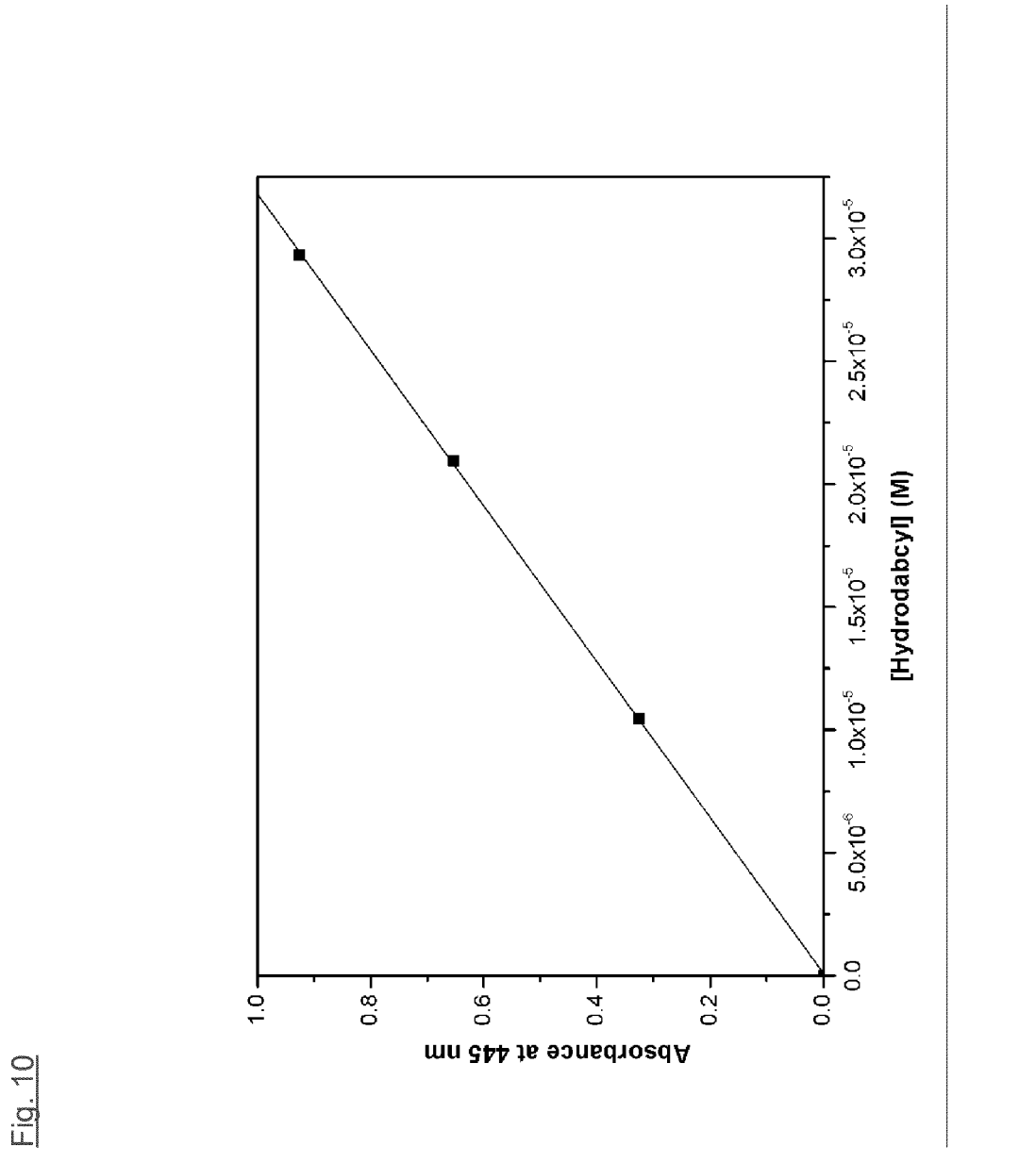
FIG. 10 shows the concentration dependence of the absorbance at 445 nm of Hydrodabcyl in 50 mM sodium phosphate (NaP) buffer pH=6.0 at T=20° C.

The linear increase of the absorbance with the concentration of the solute according to the Lambert-Beer law indicates that the stock solution is homogeneous. The result at pH 6 (lower limit for the solubility in case of direct preparation) is shown in FIG. 10, which shows the concentration dependence of the absorbance at 445 nm of Hydrodabcyl in 50 mM NaP buffer pH=6.0 at T=20° C.

Figure 11:
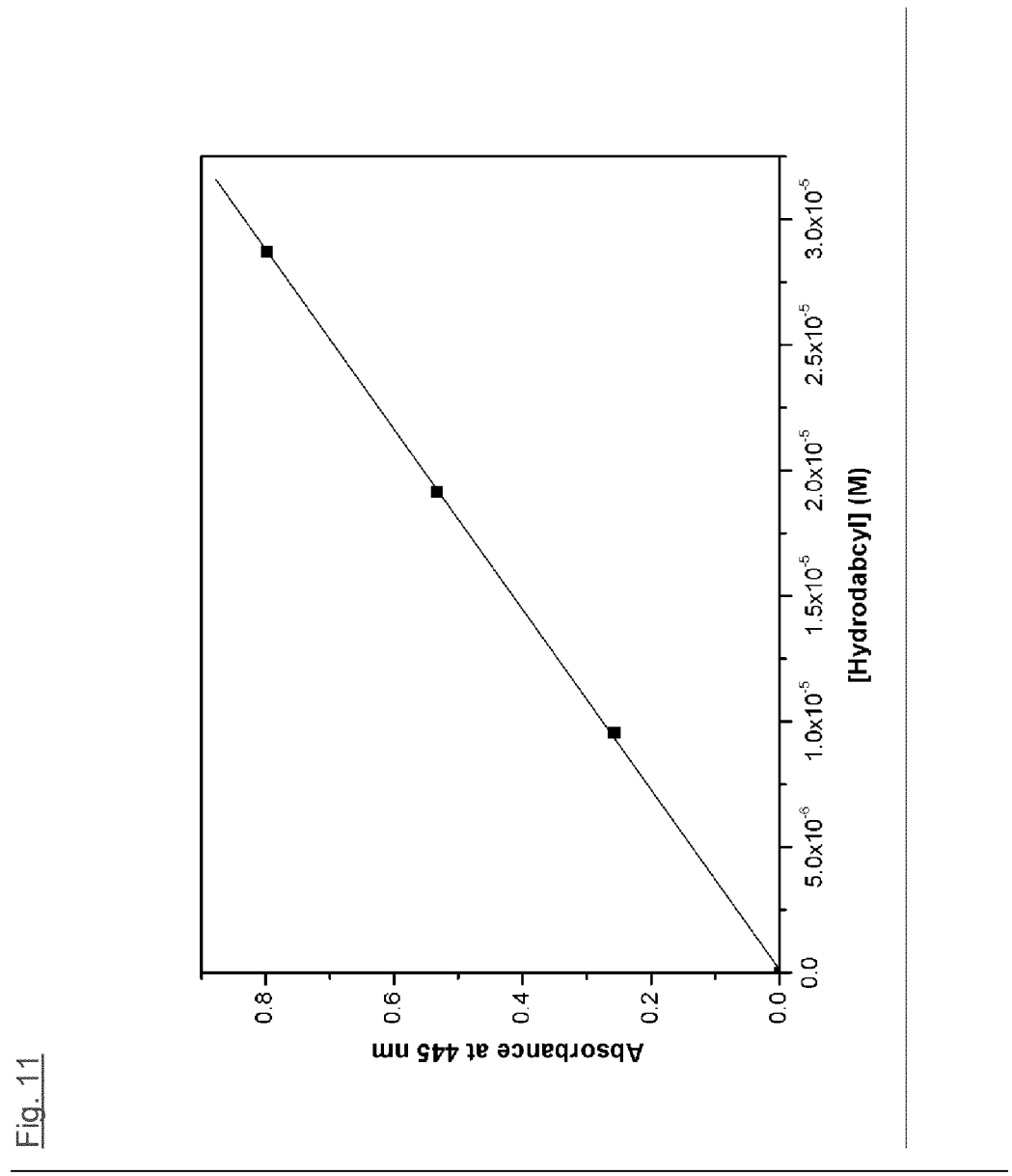
FIG. 11 shows the concentration dependence of the absorbance at 445 nm of Hydrodabcyl in 50 mM sodium phosphate (NaP) buffer pH=4.3 (obtained from pH 7.0 with 5M HCl) at T=20° C. At pH<4.3 Hydrodabcyl precipitates.

To reach complete solubility at pH<6.0, the pH of the stock solution (5 mM range) at pH 7.0 was decreased at the desired value with few drops of 5M HCl. Following gradual acidification of the medium the mM solution of Hydrodabcyl remained clear till pH 4.3. With the same procedure described above, solubility of Hydrodabcyl could be proven till pH 4.3 The result at pH 4.3 (lower limit for the solubility obtained with gradual acidification of the medium) is shown in FIG. 11 as an example, which shows concentration dependence of the absorbance at 445 nm of Hydrodabcyl in 50 mM NaP buffer pH=4.3 (obtained from pH 7.0 with 5M HCl) at T=20° C. At pH<4.3 Hydrodabcyl precipitates.

Example 8: Stability Under Light Exposure

Figure 12:
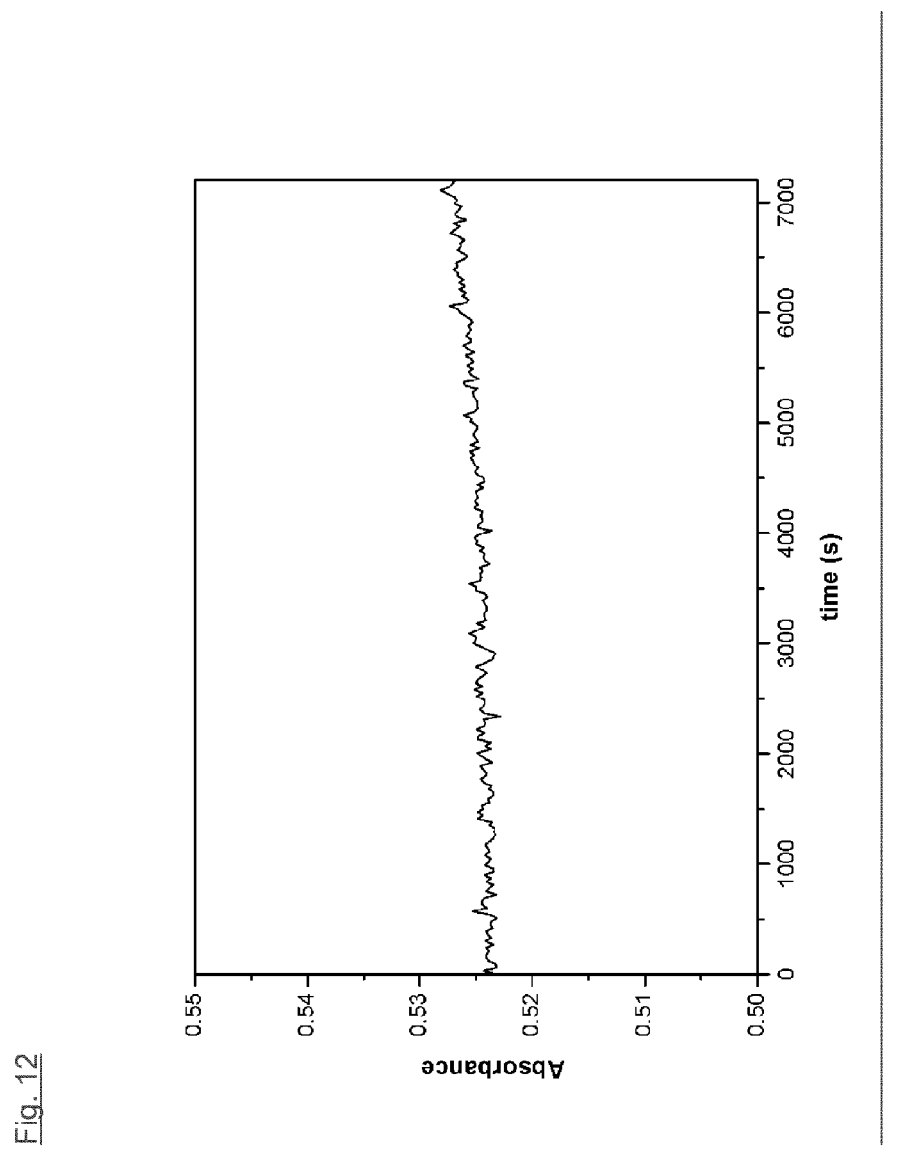
FIG. 12 shows absorbance at 470 nm of Hydrodabcyl, 14 μM in DMSO T=20° C., monitored over 2 h (7200 s).
Figure 13:
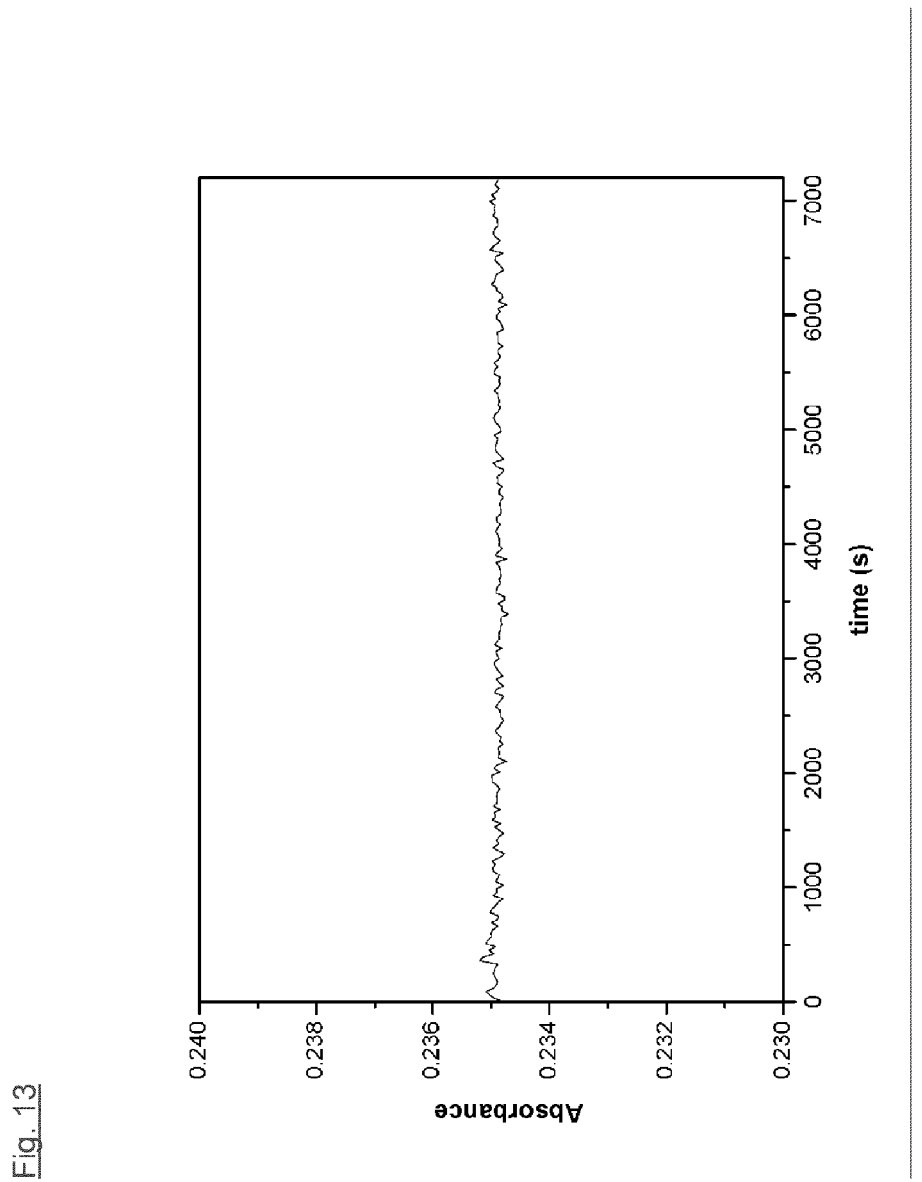
FIG. 13 shows absorbance at 451 nm of dabcyl, 7 μM in DMSO T=20° C., monitored over 2 h (7200 s).

The effect of exposure to the light beam of a commercial spectrophotometer was tested to mimic the common experimental condition. A 2-hour long continuous irradiation at a wavelength corresponding to the maximum of absorption in DMSO of a solution of Hydrodabcyl and one of dabcyl provided a constant signal, indicating that the absorption properties under these conditions are not affected for both compounds. These findings can be seen in FIGS. 12 and 13 showing absorbance at 470 nm of Hydrodabcyl, 14 μM in DMSO T=20° C., monitored over 2 h (7200 s), and absorbance at 451 nm of dabcyl, 7 μM in DMSO T=20° C., monitored over 2 h (7200 s).

Figure 14:
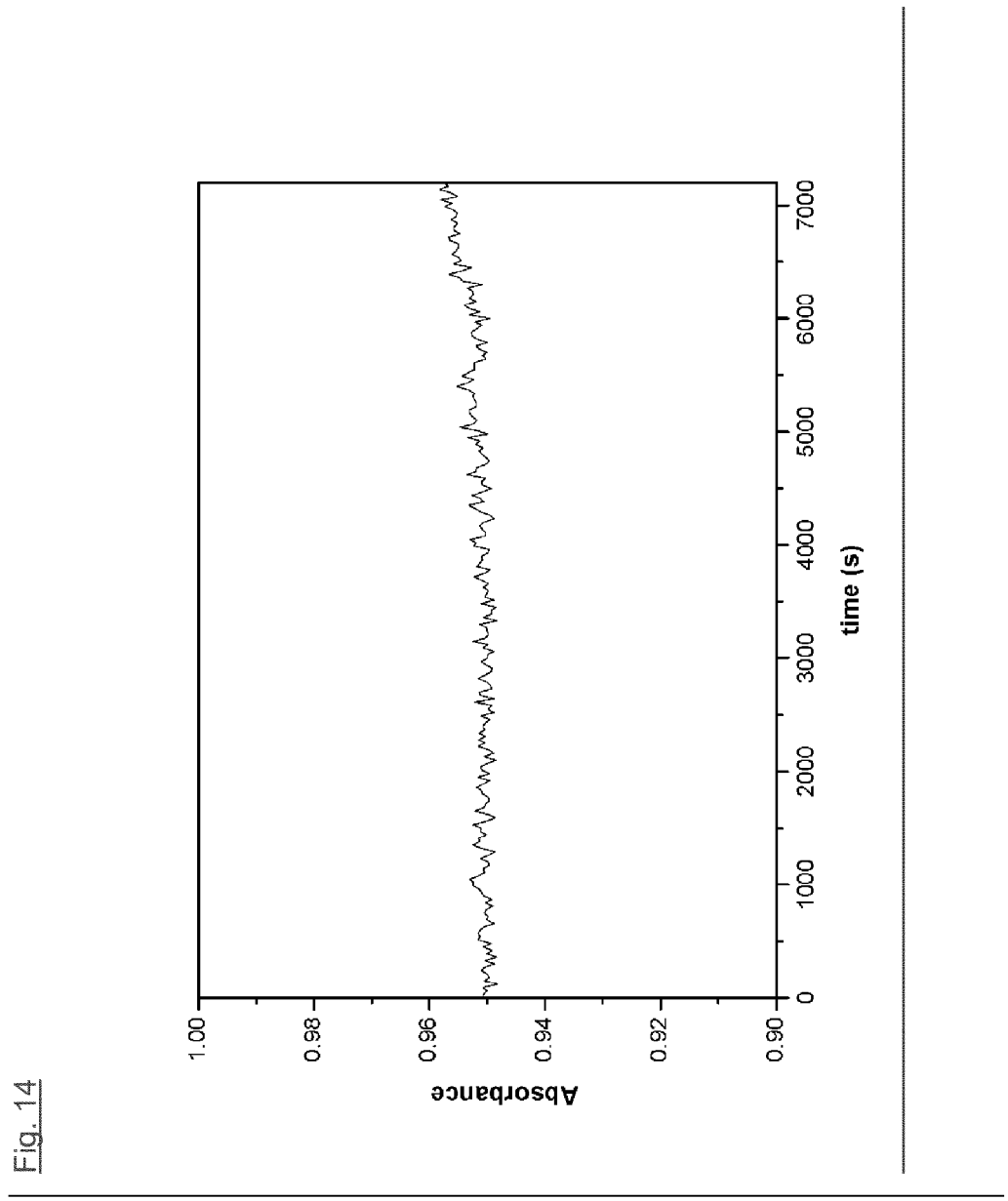
FIG. 14 shows absorbance at 445 nm of Hydrodabcyl, 22 μM in buffered aqueous solution pH=8 T=20° C., monitored over 2 h (7200 s).

Additionally, in the case of Hydrodabcyl, stability under a 2-hour long irradiation is observed also in buffered aqueous solution pH8. This is shown in FIG. 14, showing absorbance at 445 nm of Hydrodabcyl, 22 μM in buffered aqueous solution pH=8 T=20° C., monitored over 2 h (7200 s).

However, Hydrodabcyl is much more stable under light exposure than dabcyl. One solution of dabcyl and one of Hydrodabcyl, both at 17.5 μM in DMSO prepared in the dark, were exposed for 5 minutes to the light of a common 60 W tungsten lamp. This relatively short time of exposure was enough to strongly modify the absorption spectrum of dabcyl, whereas it had no effect on the absorption spectrum of Hydrodabcyl. The original spectrum of dabcyl could be recovered only after 10 min in the dark (see FIGS. 15 and 16).

REFERENCES

[1] Gershkovich A. A. & Kholodovych V. V. Fluorogenic substrates for proteases based on intramolecular fluorescence energy transfer (IFETS). *J. Biochem. Biophys. Methods* 1996, 33, 135-162.

[2] Mayatoshi E. D., Wang G. T., Kraft G. A. & Erickson J. Novel fluorogenic substrates for assaying retroviral proteases by resonance energy transfer. *Science*, 1990, 247, 954-958;

[3] Tyagy S. & Kramer F. R. Molecular Beacons: probes that fluoresce upon hybridization. *Nat. Biotech.* 1996, 14, 303-308.

[4] Holskin B P., Bukhtiyarova M., Dunn, B. M., Baur P., de Chastonay J. & Pennington M. W. A continuous fluorescence-based assay of human cytomegalovirus protease using a peptide substrate. *Anal. Biochem.* 1995, 226, 148-155.

[5] Loudwig S. & Bayley H. Protoisomerization of an individual azobenzene molecule in water: an on-off switch triggered by light at a fixed wavelength. *J. Am. Chem. Soc.* 2006, 126, 12404-12405

[6] Petrzilka T. & Lusuardi W. G. *HELVETICA CHIMICA ACTA*, 1973, 56, 515.

[7] Christie, R. M. Colour Chemistry. Cambridge: Royal Society of Chemistry: Cambridge 2001.

[8] Handbook of Chemistry and Physics 85$^{th}$ Ed. 2004-2005, CRC Press, David R. Lide Editor-in Chief

The invention claimed is:

1. A compound having formula (I)

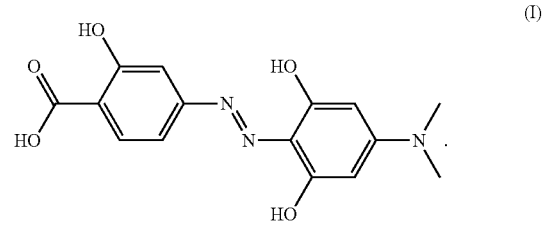 [SMILES: CN(C)c1cc(O)c(/N=N/c2ccc(C(=O)O)c(O)c2)c(O)c1]

(I)

2. Method of producing a compound having formula (I)

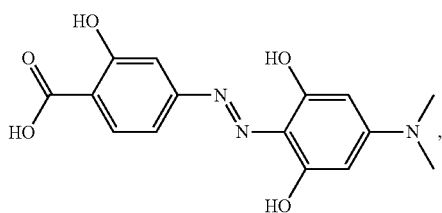

wherein the method comprises the steps of
a) producing 5-dimethylamino-resorcinol (5-(dimethyl-amino)benzene-1,3-diol)

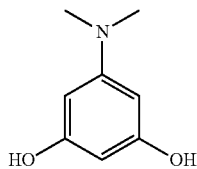

by reacting phloroglucinol (benzene-1,3,5-triol) with dimethylamine (HN(CH$_3$)$_2$) to obtain 5-dimethyl-amino-resorcinol; and
b) azo-coupling 4-diazo-salicylic acid to 5-dimethyl-amino-resorcinol to obtain the compound having formula (I).

3. Method of claim 2 further comprising step a1), wherein the compound obtained in step a) of claim 2 is purified by
(i) concentrating the 5-dimethylamino-resorcinol;
(ii) purifying the residue obtained in step (i) by column chromatography; and
(iii) crystallizing the purified compound obtained in step (ii).

4. Method of claim 2, wherein 4-diazo-salicylic acid is obtained by reacting 4-aminosalicylic acid with NaNO$_2$ and HCl to obtain a 4-diazo-salicylic acid having the formula:

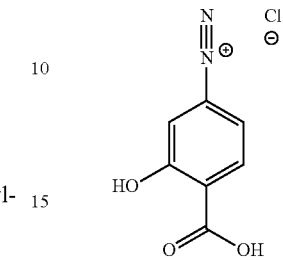

5. Method of claim 2, wherein the method further comprises a step b1), wherein the compound obtained in step b) of claim 2 is purified by precipitation at pH<4 followed by centrifugation.

6. A probe comprising a reporter and the compound of claim 1.

7. A method of measuring fluorescence comprising administering a probe comprising a reporter and the compound of claim 1 to a sample and measuring the fluorescence of the sample, wherein substantially no fluorescence is observed from the compound of claim 1.

8. The method of claim 7, wherein the sample is a biological system.

9. The method of claim 8, wherein the administering is in vivo.

10. The method of claim 8, wherein the administering is in vitro.

* * * * *